United States Patent [19]

Hammock et al.

[11] Patent Number: 4,562,292
[45] Date of Patent: Dec. 31, 1985

[54] TRIFLUOROMETHYLKETONE SULFIDES AND REVERSIBLE ENZYME INHIBITION THEREWITH

[75] Inventors: Bruce D. Hammock, Davis, Calif.; Christopher A. Mullin, State College, Pa.

[73] Assignee: The Regents of the University of California, Berkeley, Calif.

[21] Appl. No.: 524,528

[22] Filed: Aug. 18, 1983

[51] Int. Cl.⁴ .................................................. C07C 151/00
[52] U.S. Cl. ....................... 568/043; 568/23; 568/25; 568/308
[58] Field of Search ................ 568/31, 20, 23, 25, 568/37, 43, 63, 308, 303, 383

[56] References Cited

U.S. PATENT DOCUMENTS

| | | | |
|---|---|---|---|
| 2,834,707 | 5/1958 | Smith et al. | 167/22 |
| 2,974,086 | 3/1961 | Beroza et al. | 568/38 |
| 3,356,566 | 12/1967 | Goodhue et al. | 167/22 |
| 3,389,181 | 6/1968 | Merritt | 568/419 |
| 3,689,659 | 9/1972 | Langkammerer | 424/275 |
| 3,748,361 | 7/1973 | Rosenfeld et al. | 560/38 |
| 3,787,443 | 1/1974 | Erickson | 568/38 |
| 3,856,750 | 12/1974 | Guillory et al. | 568/20 |
| 3,879,429 | 4/1975 | Chodnekar et al. | 568/38 |
| 3,935,271 | 1/1976 | Schelling et al. | 568/38 |
| 3,937,738 | 2/1976 | Throckmorton | 568/38 |
| 3,944,531 | 3/1976 | Chodnekar et al. | 568/27 |
| 3,965,190 | 6/1976 | Guidicelli et al. | 568/27 |
| 4,001,339 | 1/1977 | Chodnekar et al. | 568/626 |
| 4,020,169 | 4/1977 | Remy et al. | 568/31 |
| 4,140,794 | 2/1979 | Piccardi et al. | 424/282 |
| 4,172,851 | 10/1979 | Childs | 424/331 |
| 4,225,619 | 9/1980 | Brickl et al. | 424/331 |
| 4,229,470 | 10/1980 | Piccardi et al. | 424/304 |
| 4,243,683 | 1/1981 | Broughton et al. | 424/331 |
| 4,322,441 | 3/1982 | Engel et al. | 424/331 |
| 4,347,256 | 8/1982 | Bowers | 424/331 |
| 4,358,308 | 11/1982 | Swithenback | 568/43 |
| 4,371,708 | 2/1983 | Kramer et al. | 568/31 |

OTHER PUBLICATIONS

Hammock et al., *Pestic. Biochem. Physiol.* 17 76-88 (1982).

*Primary Examiner*—Werren B. Lone
*Attorney, Agent, or Firm*—Majestic, Gallagher, Parsons & Siebert

[57] ABSTRACT

Novel compounds are provided which have the formula

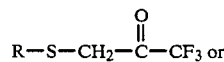

or

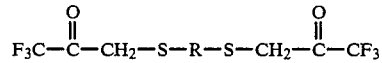

where R is a substituent having at least five multivalent atoms. The compounds are reversible inhibitors of hydrolytic enzymes, and offer potential as drug and pesticide synergists and antagonists. Some are extremely potent inhibitors of juvenile hormone esterases. The compounds having the single 1,1,1-trifluoro-3-substituted thiopropan-2-one moiety can be immobilized to solid supports and used as ligands in affinity chromatography.

13 Claims, No Drawings

TRIFLUOROMETHYLKETONE SULFIDES AND REVERSIBLE ENZYME INHIBITION THEREWITH

This invention was made with Government support under Grant Nos. 5-RO-1-ES02710-01 and ES-000107 awarded by the Department of Health and Human Services. The Government has certain rights in this invention.

FIELD OF THE INVENTION

The present invention generally relates to trifluoromethylketones, and more particularly to novel trifluoromethylketone sulfides useful as reversible inhibitors of hydrolytic enzymes, such as serine esterases and amidases.

BACKGROUND OF THE INVENTION

Various compounds which inhibit, or bind to, enzymes are known and have a broad range of in vitro and in vivo applications. For example, ligands immobolized to solid-phase supports which reversibly bind to enzymes are useful in affinity chromatography to purify enzymes and to separate them from biological fluids.

Among the hydrolytic enzymes are serine esterases and amidases. Juvenile hormone esterase is, for example, one of the serine esterases. Compounds which inhibit juvenile hormone esterase have received considerable interest as selective insert control agents, since juvenile hormones regulate a great number of reproductive and developmental events in insects and juvenile hormone esterase mediate the metabolism of the juvenile hormones.

Certain phosphoramidates have been found to inhibit juvenile hormone esterases. In particular, O-ethyl-S-phenyl phosphoramidothiolate (hereinafter "EPPAT") has been found to display potent in vitro inhibition of juvenile hormone esterase and topical application has been shown to disrupt development of the cabbage looper. See, e.g. Sparks and Hammock, *Pestic. Biochem, Physiol.* 14, 290 (1981).

Several trifluoromethylketones have recently been found to be potent inhibitors of crude juvenile hormone esterase from the cabbage looper in vitro. The most potent of these (1,1,1-trifluorotetradecan-2-one, hereinafter abbreviated "TFT") was found to display relatively greater juvenile hormone esterase activity in vitro than EPPAT. However, TFT displayed a lack of pronounced in vivo activity when applied topically to cabbage looper (Noctuidae, *Trichoplusia ni*). Hammock et al., *Pestic. Biochem. Physiol.* 17, pp. 76-88 (1982).

SUMMARY OF THE INVENTION

Accordingly, it is an object of the present invention to provide slowly reversible inhibitors of hydrolytic enzymes, such as serine esterases and amidases, which are useful for various in vivo and in vitro applications.

It is a further object of the present invention to provide extremely potent inhibitors of juvenile hormone esterases which have in vivo activity. It is yet a further object of the present invention to provide reversible inhibitors of human neurotoxic esterase, and other esterases and amidases of toxicological and pharmacological significance.

In one aspect of the present invention, a novel compound has the formula

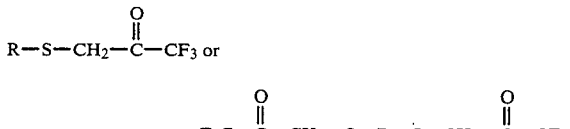

wherein R is an alkyl, alkenyl, alkynyl, aryl, or arylalkyl substituent having at least 5 multivalent atoms, more preferably wherein R is an alkyl, alkenyl, or alkynyl substituent having from 8 to about 12 carbon atoms. The substituent may include nitrogen, selenium, sulfur or oxygen.

One particularly preferred embodiment is

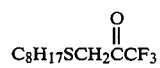

sometimes hereinafter referred to as "TFPOS".

Compounds in accordance with the subject invention are useful for reversibly binding a variety of hydrolytic enzymes, such as serine esterases and amidases. Some of the novel compounds, including TFPOS, are extremely potent inhibitors of juvenile hormone esterases with an inhibition $I_{50}$ value in the nanomolar range. ($I_{50}$ is defined as the concentration of a compound required to inhibit 50% of an enzyme's activity.) For example, TFPOS is over 40 times more active in vitro for juvenile hormone esterase than the prior known TFT, and TFPOS of the invention has pronounced in vivo activity. Some of the novel compounds are extremely potent, but reversible, inhibitors of human neurotoxic esterase, and may find application by preventing, or being used as antidotes of, delayed neurotoxicity. They inhibit human clofibrate esterase and rodent malathion esterase and may act as drug and pesticide synergists or antagonists.

BEST MODE OF PRACTICING THE INVENTION

Compounds in accordance with the present invention have the formula as shown by FIG. I(A), below.

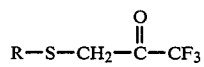

FIG. I(A)

wherein R is an alkyl, alkenyl, alkynyl, aryl, or arylalkyl substituent having at least 5 multivalent atoms. The structure shown as FIG. I(A) will sometimes hereinafter be referred to as the "monoalkylated" compound.

The inventive compounds have a sulfide bond beta to a carbonyl. Analysis by X-ray crystallography has indicated that the sulfur atom is hydrogen bonded to the carbonyl when hydrated. It is believed that the sulfur atom of the novel compounds may stabilize the inhibitory form and contribute to the surprising potency of the compounds with respect to previously known trifluoromethylketones (such as TFT). It is also believed that the inhibitory activity of the inventive compounds on serine esterases and amidases may be due to their formation of hemiketals with the serine present at the enzyme catalytic site, and that the carbon-fluorine bonds may enhance the rate of bioabsorption for in vivo uses.

As shown by FIG. I(A), the novel compounds all have a trifluoromethyl group bonded to the carbonyl, the beta sulfur, and a substituent bonded to the sulfur, distal with respect to the carbonyl, having at least 5 multivalent atoms. By "multivalent" is meant an atom which forms 2 or more covalent bonds. The multivalent atoms of the R substituent will sometimes be all carbon atoms, and normally be a majority of carbon atoms which also includes one or more nitrogen, selenium, sulfur, and oxygen atoms.

Activity of the inventive compounds for enzyme inhibition is believed to be affected by molecular volume, or "bulk" of the R substituent, with activity decreasing when molar refractivity values (used as a physiochemical parameter) are either larger or smaller than those wherein the R substituent has at least 5 to about 13 multivalent atoms. However, R substituents having greater than about 13 multivalent atoms may be useful in providing inhibitors for various hydrolytic enzymes.

Preferred alkyl substituents have from 8 to about 12 carbon atoms, and may be either branched or unbranched chains. A particularly preferred alkyl substituent is n-octyl. Preferred alkyl substituents including sulfur have from four to twelve carbon atoms, and those including oxygen preferably have about 10 carbon atoms. Alkenyl and alkynyl substituents also may be branched or unbranched, and particularly preferred alkenyl and alkynyl substituents have about 10 or 11 carbon atoms, and may include a terminal methoxy group.

Suitable monocyclic substituents include cyclohexyl, phenyl and benzyl, either non-substituted or substituted, with a halogen or an alkyl.

Compounds in accordance with the present invention may also have the formula as shown by FIG. I(B), below.

$$F_3C-\overset{O}{\underset{\|}{C}}-CH_2-S-R-S-CH_2-\overset{O}{\underset{\|}{C}}-CF_3 \qquad \text{FIG. I(B)}$$

wherein R is as previously described. The structure shown as FIG. I(B) will sometimes hereinafter be referred to as the "dialkylated" compound. As may be seen by comparing FIG. I(A) with FIG. I(B), the former structure differs from the latter by having a single 1,1,1-trifluoro-3-substituted thiopropan-2-one moiety instead of two. In affinity chromatography applications, the FIG. I(A) structure is the best mode contemplated for carrying out the paresent invention, as more fully described hereinafter.

Table I below illustrates structures for a number of the inventive compounds which have been prepared.

TABLE I

| Reference No. | Structure |
|---|---|
| 1. | $C_8H_{17}SCH_2\overset{O}{\underset{\|}{C}}CF_3$ |
| 2. | $C_9H_{19}SCH_2\overset{O}{\underset{\|}{C}}CF_3$ |
| 3. | $C_{10}H_{21}SCH_2\overset{O}{\underset{\|}{C}}CF_3$ |

TABLE I-continued

| Reference No. | Structure |
|---|---|
| 4. | $C_{11}H_{23}SCH_2\overset{O}{\underset{\|}{C}}CF_3$ |
| 5. | $C_{12}H_{25}SCH_2\overset{O}{\underset{\|}{C}}CF_3$ |
| 6. | cyclohexyl-$SCH_2\overset{O}{\underset{\|}{C}}CF_3$ |
| 7. | phenyl-$CH_2SCH_2\overset{O}{\underset{\|}{C}}CF_3$ |
| 8. | phenyl-$SCH_2\overset{O}{\underset{\|}{C}}CF_3$ |
| 9. | 2-$CH_3$-phenyl-$SCH_2\overset{O}{\underset{\|}{C}}CF_3$ |
| 10. | 3-$CH_3$-phenyl-$SCH_2\overset{O}{\underset{\|}{C}}CF_3$ |
| 11. | 4-$CH_3$-phenyl-$SCH_2\overset{O}{\underset{\|}{C}}CF_3$ |
| 12. | 2-isopropyl-phenyl-$SCH_2\overset{O}{\underset{\|}{C}}CF_3$ |
| 13. | 4-$tC_4H_9$-phenyl-$SCH_2\overset{O}{\underset{\|}{C}}CF_3$ |
| 14. | 2-$CH_3O$-phenyl-$SCH_2\overset{O}{\underset{\|}{C}}CF_3$ |
| 15. | 4-$CH_3O$-phenyl-$SCH_2\overset{O}{\underset{\|}{C}}CF_3$ |
| 16. | 4-F-phenyl-$SCH_2\overset{O}{\underset{\|}{C}}CF_3$ |
| 17. | 2-Cl-phenyl-$SCH_2\overset{O}{\underset{\|}{C}}CF_3$ |
| 18. | 3-Cl-phenyl-$SCH_2\overset{O}{\underset{\|}{C}}CF_3$ |
| 19. | 4-Cl-phenyl-$SCH_2\overset{O}{\underset{\|}{C}}CF_3$ |

TABLE I-continued

| Reference No. | Structure |
|---|---|
| 20. | Br-C6H4-SCH2C(O)CF3 |
| 21. | 3-CF3-C6H4-SCH2C(O)CF3 |
| 22. | 2,5-Cl2-C6H3-SCH2C(O)CF3 |
| 23. | 3,4-Cl2-C6H3-SCH2C(O)CF3 |
| 24. | 2,4,5-Cl3-C6H2-SCH2C(O)CF2 |
| 25. | 2-Naphthyl-SCH2C(O)CF3 |
| 26. | HS(CH2)4SCH2CF3 |
| 27. | HS(CH2)10SCH2CF3 |
| 28. | 2-Pyridyl-SCH2C(O)CF3 |
| 29. | 4-Pyridyl-SCH2C(O)CF3 |
| 30. | 8-Quinolinyl-SCH2C(O)CF3 |
| 31. | CH3C(CH3)=CH(CH2)2C(CH3)=CH(CH2)2SCH2C(O)CF3 |
| 32. | CH3C(CH3)(OCH3)(CH2)3C(CH3)=CH(CH2)2SCH2C(O)CF3 |
| 33. | CH3C(CH3)(OCH3)(CH2)3CH(CH3)(CH2)2SCH2C(O)CF3 |
| 34. | (CH3)2C=CH(CH2)2CH(CH3)(CH2)2SCH2C(O)CF3 |
| 35. | F3C-C(O)-CH2-S-C6H4-O-C6H4-S-CH2-C(O)-CF3 |

Illustrative properties and representative preparations of compounds in accordance with the present invention are more fully described as follows.

EXPERIMENTAL

The following experimental methods, materials and results are described for purposes of illustrating the present invention. However, other aspects, advantages and modifications within the scope of the invention will be apparent to those skilled in the art to which the invention pertains.

Generally, most compounds in accordance with the present invention may be prepared by the reaction of the appropriate thiol with 3-bromo-1,1,1,-trifluoropropan-2-one (hereinafter referred to as "BTFA"), available from PCR Research Chemicals, Inc. Gainesville, Fla. After preparation and when appropriate, the compounds may be purified by distillation, recrystallization, preparative TLC or column chromatography.

After preparation, compounds such as those illustrated in Table I, above, were typically tested for enzyme inhibitory activity with several hydrolytic enzymes as follows.

JH esterase activity was monitored in the hemolymph collected from last stadium day two larvae of the cabbage looper, *Trichoplusia ni*, Lepidoptera, Noctuidae. The plasma was diluted (v/v) in sodium phosphate buffer (pH 7.4, 0.08M with 0.01% [w/v] phenylthiourea) and frozen at $-60°$ C. until used. The inventive compounds were added in 1$\mu$ liter of ethanol to 100$\mu$ liters of the diluted plasma and preincubated for 10 min at 30° C. before adding substrate (ClO$^3$H JH III New England Nuclear and unlabeled E, E JH III, Calbiochem) in 1$\mu$ liter of ethanol to give a final concentration of $5\times10^{-6}$ M JH III containing about 30,000 dpm/assay (Hammock and Sparks, *Anal. Biochem.* 82, 573 (1977).

$\alpha$-Naphtyl acetate ($\alpha$-NA) hydrolysis was monitored similarly in the hemolymph of prepupae of *T. ni* (fifth stadium, day 4) with a final substrate of $2.3\times10^{-4}$M. Plasma dilutions and incubation times were chosen to give a hydrolysis rate which was linear with time.

For acetylcholinesterase (AChE) activity, 20$\mu$ liters of acetylthiocholine iodide (Sigma) in sodium phosphate buffer (0.05M, ph 7.2) was added to Type VI-S electric eel AChE (Sigma, 10 ng with 2-400 units/mg protein) in 3 ml the same buffer to give a final substrate concentration of $5\times10^{-4}$M. The assay was run at 37° C.

For trypsin, 1.5 ml of p-toluenesulfonyl-L-arginine methyl ester (Sigma) in Tris HCl buffer (pH 8.1, 0.04M with 0.1M $CaCl_2$) was added to 1.5 ml of the same buffer containing bovine pancreatic type III trypsin (Sigma, 0.24 μg) to give a final substrate concentration of $1\times10^{-4}$M. The assay was performed at 25° C.

For α-chymotrypsin activity (α-ChT), 50μ liters of p-nitrophenyltrimethylacetate (Aldrich) in acetonitrile was added to the enzyme solution to give a final substrate concentration of $5.8\times10^{-5}$M. The enzyme solution was prepared immediately before the assay by adding 0.1 ml of bovine pancreas Type II—chymotrypsin (Sigma, 1.7 μg with 40-50 units/mg protein) in sodium acetate buffer (0.01M, pH 4.6) to 2.95 ml of sodium phosphate buffer (0.1M. pH 8.0) at 25° C. Enzyme concentrations and incubation times were selected to give linear hydrolysis rates with time.

For AChE, trypsin and α-ChT, the inhibitor was added to ethanol 10 min prior to the substrate and preincubated at the same temperature used for the actual assay. In no case was greater than 1% v/v ethanol added, and ethanol controls were always run. For the spectrophotometric enzyme assays, initial studies were run on a Varian-Cary 219 UV/visible spectrophotometer, while subsequent assays were run on a Gilford manual EIA reading using disposable cuvettes.

In each case, at least three replicates of each inhibitor concentration were used. A minimum of two inhibitor concentrations showing greater and less than 50% inhibition were used to determine the $I_{50}$ values from semi-log plots except in the case of weaker inhibitors. Only those points on the apparently linear portion of the curve were used to calculate the $I_{50}$'s.

Table II, below, illustrates enzyme assay data for four hydrolytic enzymes for various of the inventive compounds by the above-described protocol.

TABLE II

| Compound Ref. No. (same as Table I) | JHE | $I_{50}$ (M) α-NAE | AChE | Trypsin (*greater than) |
|---|---|---|---|---|
| 1. | $2.3 \times 10^{-0}$ | $1.2 \times 10^{-6}$ | $2.3 \times 10^{-6}$ | $*1 \times 10^{-5}$ |
| 2. | $3.7 \times 10^{-9}$ | $6.3 \times 10^{-6}$ | $9.3 \times 10^{-7}$ | $*1 \times 10^{-4}$ |
| 3. | $2.0 \times 10^{-8}$ | $1.0 \times 10^{-5}$ | $3.2 \times 10^{-6}$ | $8.2 \times 10^{-5}$ |
| 4. | $4.3 \times 10^{-8}$ | $4.5 \times 10^{-5}$ | $2.6 \times 10^{-6}$ | $*1 \times 10^{-4}$ |
| 5. | $1.5 \times 10^{-8}$ | $9.7 \times 10^{-5}$ | $2.2 \times 10^{-6}$ | $*1 \times 10^{-4}$ |
| 6. | $5.2 \times 10^{-6}$ | $7.1 \times 10^{-7}$ | $1.8 \times 10^{-6}$ | $*1 \times 10^{-4}$ |
| 9. | $4.3 \times 10^{-6}$ | $6.0 \times 10^{-7}$ | $3.7 \times 10^{-7}$ | $8.5 \times 10^{-5}$ |
| 11. | $1.1 \times 10^{-7}$ | $1.6 \times 10^{-6}$ | $6.1 \times 10^{-7}$ | $*1 \times 10^{-4}$ |
| 12. | $3.4 \times 10^{-7}$ | $2.7 \times 10^{-7}$ | $4.9 \times 10^{-8}$ | $4.7 \times 10^{-5}$ |
| 20. | $4.1 \times 10^{-7}$ | $4.9 \times 10^{-6}$ | $2.4 \times 10^{-6}$ | $*1 \times 10^{-5}$ |
| 31. | $3.2 \times 10^{-9}$ | $7.2 \times 10^{-7}$ | $6.2 \times 10^{-5}$ | $*1 \times 10^{-4}$ |
| 32. | $3.1 \times 10^{-9}$ | $1.9 \times 10^{-6}$ | $*1 \times 10^{-4}$ | $*1 \times 10^{-4}$ |

The $I_{50}$'s are indicative of relative inhibitory potency. They indicate that by varying the R group in the general structure shown by FIG. I one can obtain selective inhibition of a variety of different enzymes.

Various of the inventive compounds were also tested for reversible inhibition with neurotoxic esterase, as described below, with data illustrated by Table III.

TABLE III

| Compound Reference # | Protective Concentration at ½k (Velocity Constant in $Min^{-1}$)(M) |
|---|---|
| 16 | $1.35 \times 10^{-6}$ |
| 9 | $1.1 \times 10^{-6}$ |
| 12 | $6.2 \times 10^{-7}$ |
| 4 | $4.2 \times 10^{-7}$ |
| 20 | $3.5 \times 10^{-7}$ |
| 5 | $2.3 \times 10^{-7}$ |
| 3 | $1.7 \times 10^{-7}$ |
| 2 | $1.1 \times 10^{-7}$ |
| 11 | $1 \times 10^{-7}$ |
| 10 | $9 \times 10^{-8}$ |
| 1 | $6 \times 10^{-8}$ |
| 26 | $3 \times 10^{-8}$ |
| 27 | $1.2 \times 10^{-8}$ |

Neurotoxic esterase is found in nervous tissue. When this enzyme is irreversibly inhibited (such as by means of certain antioxidants in contaminated cooking oil or food contaminated by certain insecticides), the myelin sheath is lost which leads to an incurable syndrome known as delayed neurotoxicity. A compound with reversible binding to neurotoxic esterases should prevent this syndrome and hold potential as an antidote.

The data in Table III were generated by determining what concentration of the various novel compounds were needed to block the inhibition of human brain neurotoxic esterase by a high concentration of mepafox. Mepafox is a potent delayed neurotoxic agent which irreversibly inhibits neurotoxic esterase. These data indicate that the novel compounds can prevent the delayed neurotoxicity syndrome by preventing mepafox binding until the mepafox was metabolized, and then reversing before the toxic lesion evolves. It is believed that dialkylated compounds in accordance with the present invention may be particularly useful in blocking neurotoxic esterase, as reference compound #35 of Table I has been found to be the most potent to date. These data also indicate that the novel monoalkylated compounds can be used to purify neurotoxic esterase, as in affinity chromatography. This suggests the novel compounds will also prevent phosphorylation of acetylcholine esterase by irreversible inhibitors.

Examples I through VII, below, illustrate representative preparations of the inventive compounds. All temperatures are in Celsius.

EXAMPLE I 1,1,1-Trifluoro-3-thiobenzylpropan-2-one

Benzyl mercaptan (4 mmol) was transferred via syringe to a 2 cm diameter bottle sealed with a rubber septum and containing 2 ml of carbon tetrachloride under nitrogen. BTFA (5 mmol) was added dropwise via syringe while the reaction was stirred magnetically. The reaction was allowed to proceed under a gentle stream of nitrogen, and the evolving hydrogen bromide gas was trapped with sodium hydroxide pellets. The reaction was monitored by TLC and the high $R_f$ starting material was found to rapidly vanish in favor of a single low $R_f$ spot. After 24 hr 5 ml of ethyl ether was added and the reaction mixture washed twice with 5% w/v aqueous sodium bicarbonate and once with saturated brine. The ether layer was dried ($Na_2SO_4$) and the solvent evaporated to give a faintly orange oil in 88% isolated yield which on GLC and TLC showed only a trace of the starting material. The oil was recrystallized twice from hexane to give colorless, odorless cubes of the benzylsulfide (reference #7, Table I) in 60% yield. The crystals rapidly turned orange with the release of benzyl mercaptan upon exposure to air. MP 60°–61° C.; NMR ($CCl_3D$) 2.93, 3.35, and 3.80 ($3_s$, 2, $CH_2C(OH)_2$ or C=O) δ4.05 (s, 2, CH$_2$ phenyl), 7.45 (s, 5, phenyl); IR (neat, AgCl) 3500 (br s), 1775 (w), 1750 (s) 1175 (br s).

EXAMPLE II

1,1,1-Trifluoro-3-thiophenylpropan-2-one ("TFPPS"). Thiophenol (75 mmol) was distilled under nitrogen into a dry 50 ml flask with a stir bar. Carbon tetrachloride (10 ml) was added followed by the slow addition of BTFA (75 mmol) while the reaction mixture was held at about 20° C. with a water bath. Following the addition of BTFA, the reaction was run as before and appeared to be complete within four hours. The reaction mixture was washed as before, dried and the ether layer concentrated to give a quantitative yield of a clear oil showing approximately 12% starting material by GLC. The clear, colorless oil was distilled to give the phenyl-sulfide (reference #8 in Table I) in 83% isolated yield. Following storage at −5° C., white needles formed in the oil. bp 65.0°–65.5° C. at 2.9 mmHg; NMR (CCl$_4$) δ 3.95 (s, CH$_2$), 7.4 (m, Ph); IR (neat, AgCl) 3500 (br s), 3100 (w), 1775 (w), 1750 (m), 1625 (br w), 1580 (s), 1480 (s), 1440 (s), 1200 (br s), mass spectrum, m/z (rel intensity), 220 (90), 124 (25), 123 (100), 110 (94), 109 (71), 77 (57), 69 (41), 66 (55), 65 (44), 58 (84). The compounds illustrated as reference #25 and #20 in Table I were prepared by a similar procedure.

EXAMPLE III

1,1,1-Trifluoro-3-thioocytylpropan-2-one ("TFPOS"). The octylsulfide (TFPOS) was prepared in a protocol similar to Example II, above, except that the starting material was not distilled. Following workup the clear oil was distilled to give the product oil illustrated as reference #1 in Table I in 84% isolated yield, bp 87°–89° C. at 0.2 mm Hg. IR (neat AgCl) 3400 (br s), 2920 (s), 1770 (m), 1460 (m), 1160 (br s); mass spectrum, m/z (rel intensity) 256 (5), 199 (2), 171 (1), 145 (100), 159 (30), 129 (15), 69 (45). The compounds illustrated as reference #2, #3, #4, #5, and #6 in Table I were prepared by a similar procedure.

Many of the reaction parameters indicated in Examples I–III above can be varied. For example, although the procedure in which carbon tetrachloride was used as solvent with the reaction being driven by the evolution of hydrogen bromide gave consistently high yields in those cases in which the starting materials were soluble, benzene can be used as an alternative if the addition of BTFA is followed by the very slow addition of triethylamine. Use of benzene has resulted in only slightly lower yields. However, significantly reduced yields were obtained when pyridine or triethylamine were used as solvent, when equimolar amounts of these bases were added to benzene or carbon tetrachloride before the addition of the BTFA, or when the sodium salt of the thiol was exposed to BTFA in glyme.

Use of methanol or dichloroethane as the solvent, with sodium bicarbonate as the base, also gives consistently high yields and offers some advantages when working with compounds that are poorly soluble in carbon tetrachloride. Preparation of TFPPS in carbon tetrachloride and in methanol resulted in compounds with apparently identical properties on TLC, IR and GLC and indistinguishable slopes and I$_{50}$'s when tested as inhibitors of juvenile hormone esterase. Cooling seemed not to influence the reactions run on scales of 10 mmole. or smaller; however, water baths and slow addition of BTFA were important on larger scale reactions.

Compounds in accordance with the present invention may include heterocyclic moieties, such as cyclostructures including nitrogen, and preparation of a representative several are illustrated by Example IV, below.

EXAMPLE IV

BTFA was reacted with 8-mercaptoquinoline, 4-mercaptopyridine and 2-mercaptopyridine respectively in anhydrous methanol with sodium bicarbonate, followed by addition of 0.2M aqueous NaOH and extraction with ether, to yield the three compounds illustrated as reference #28, #29 and #30, respectively, in Table I.

Compounds in accordance with the present invention may include unsaturated and branched chains, and two representative preparations are illustrated in Example V, below.

EXAMPLE V

(E)-8,12-dimethyl-4-thia-1,1,1-trifluorotrideca-7,11-dien-2-one ("DTFT") and 7,11-dimethyl-4-thia-1,1,1-trifluorododec-10-en-2-one Homogeraniol may be prepared from geraniol by bromination, cyanide homologation, hydrolysis, and hydride reduction, as described by Hoye et al., J. Org. Chem. 43, 3693 (1978). Homogeraniol may then be converted to the corresponding thiol via the S-acetyl derivatives using a Mitsunobu procedure described by Volante, Tetrahedron Lett. 22, 3119 (1981). Alkylation of the thiol with excess bromotrifluoroacetone, followed by purification yields the compound illustrated as reference #31 in Table I. $^1$H-NMR, 5.00 (m, H-9), 3.40 (s, H-3), 2.40 (t, H-5), 1.93 (s, H-15), 1.62, 1.55 (s,s, H-13,14).

Thiols prepared from the corresponding alcohols via the S-acetyl derivatives using the Mitsunobu procedure are exemplified by the conversion of citronellol to citronellylthiol (3,7-Dimethyl-6-octene-1-thiol) as follows. 5.3 ml (0.027 mol) of di(isopropyl)azodicarboxylate (DIAD) was injected into the flask containing a solution of triphenylphosphine (6.7 g, 0.027 mol) in 100 ml of dry THF which was stirred efficiently at 0° C. A yellow precipitate formed at once and the suspension was stirred at 0° for 1 hour. Then a solution of 2.3 ml (0.013 mol) citronellol and 2 ml (ca. 0.027 mol) thiolacetic acid in 50 ml THF was added dropwise over 10 min into the suspension. The mixture was stirred for 2 hours (0°–20° C.), concentrated to give 6 g of residue, and kept at 4° C. for 12 hours. The liquid was decanted off and the solid part was triturated with pure hexane. The solutions were combined and purified by flash chromatography with 5% hexane-ethyl acetate. A crude product of 2.3 g (83%) of citronellyl thioacetate was obtained which was sufficiently pure for the subsequent hydrolysis. The only major contaminant was the corresponding thiol as determined by TLC (20% hexaneethyl/acetate thiolester, R$_f$=0.56; thiol, R$_f$=0.67. Flash chromatography (2% hexane ethyl acetate) gave a homogenous product (less than 89% by GC) which was used for the spectra. IR (neat film), 2900, 1690, 1650, 1140 cm$^{-1}$; $^1$H-NMR, δ5.03 (t, J=7 Hz, H-6), 2.50 (t, J=6.5 Hz, H-1), 2.03 (s, acetyl CH$_3$); 1.94 (m, H-5); 1.65, 1.57 (s, s, H-8, H-9), 0.88 (d, J=5.8 Hz, H-10).

The crude thiolester (2.3 g, 0.011 mol) was dissolved in 25 ml ether and added dropwise to a suspension of 0.8 g of LiAlH$_4$ (0.02 mol) in 20 mL ether under N$_2$. The mixture was stirred for 2.5 hr at room temperature, and then 15 ml of 1N HCl was added to destroy the excess LiAlH$_4$. The organic layer was separated and concentrated to give 1.3 g of crude product (69%). Evaporative distillation (80°/0.05 mm Hg) gave 1.10 g of a colorless liquid (citronellythiol) which was homogeneous by TLC (15% hexane-ethyl/acetate, R$_f$=0.58). IR (neat), 2920, 2580, 1650, 1450, 1380 cm$^{-1}$; $^1$H-NMR, $\delta$5.02 (t, 7 Hz, H-6), 2.48 (t, H-1), 1.92 (m, H-5), 1.65, 1.55 (s, s, H-8, H-9), 0.88 (d, 5.5 Hz, H-10).

The alkylation conditions which minimized side products also required prolonged reaction times. Thus, 0.14 g of the citronellythiol prepared as described above (0.81 mmol) and 0.30 g (3.6 mmol) of solid NaHCO$_3$ were added to a solution of 0.18 g of 3-bromo-1,1,1-trifluoroacetone (0.95 mmol) (Columbia Organics) in 20 ml CH$_2$Cl$_2$. The mixture was stirred under N$_2$ at room temperature for 5 days and then poured into 50 ml H$_2$O. After extraction with ether and washing with brine, the solvent was evaporated to give 0.20 g of the crude trifluoromethyl ketone. Purification on a flash column and then distillation gave 0.14 g (61%) of a colorless product (reference compound 19 #43 of Table I) which lacked the $^1$H resonances ($\delta$2.85, 3.75+3.83) attributed to the hydrated form (13). $^1$H-NMR, $\delta$5.03 (t, 7 Hz, H-10), 3.44 (s, H-3), 2.50 (t, 6.4 Hz, H-5), 1.90 (m, H-9), 1.62, 1.58 (s, s, H-12, 13), 0.87 (d, 6 Hz, H-14).

Compounds of the present invention can include oxygen as at least one of the multivalent atoms, for example, in a methoxy or acetoxy group, and two representative preparations are illustrated by Example VI, below.

EXAMPLE VI 7,11-Dimethyl-11-methoxy-4-thia-1,1,1-trifluorododecan-2-one and
(E)-8,12-Dimethyl-12-methoxy-4-Thia-1,1,1-trifluorotridec-7-en-2-one Citronellol was converted to the methoxy alcohol by methoxymercuration-basic borohydride reduction, as described by Patwardhan, ete al., Agric. Biol. Chem. 40, 697 (1976). Thiolation of 5.2 g (0.028 mmol) as described in Example V, above, gave 3.0 g (0.015 mmol, 54%) of chromatographed thiol. Sodium bicarbonate-catalyzed alkylation of 90 mg (0.45 mmol of the thiol) gave 100 mg (72%) of the compound illustrated by reference #33 of Table I after chromatography and distillation. $^1$H-NMR, $\delta$3.45 (s, H-3), 3.15 (s, OCH$_3$), 2.50 (t, 8 Hz, H-5), 1.15 (s, H-12,13), 0.87 (d, 6 Hz, H-14).

Geranyl acetate was converted to (E)-3,7-dimethyl-7-methoxyoct-2-en-1-ol by methoxymercurationbasic borohydride reduction followed by chromatographic removal of the dimethoxy material. Homologation of this material to (E)-4,8-dimethyl-8-methoxynon-3-en-1-ol was accomplished as for geraniol. The alcohol (1.00 g, 5.0 mmol) was converted to the corresponding thiol (0.70 g, 3.2 mmol) in 64% yield after chromatography and distillation. Sodium bicarbonate-catalyzed alkylation of the thiol (0.090 g, 0.41 mmol) with excess bromotrifluoroacetone in CH$_2$Cl$_2$ gave 0.079 g of the compound illustrated as reference #32 in Table I (62%) after chromatography and evaporative distillation; $^1$H-NMR, $\delta$5.00 (t, 6.5 Hz, H-7), 3.42 (s, H-3), 3.10 (s, OCH$_3$), 2.3 (m, H-5), 1.45 (s, H-15), 1.13 (s, H-13, 14).

Compounds of the present invention can include sulfur as at least one of the multivalent atoms, for example in a thiol group, and representative preparations are illustrated by Example VII, below.

EXAMPLE VII

Compounds containing two thiols (such as 1,2-ethane dithiol; 1,3-propane dithiol; 1,4-butane dithiol; or 1,10-decane dithiol) were reacted with BTFA as in Examples I or IV except that equimolar BTFA was added slowly. Mono and dialkylated products were separated from each other and the starting material by preparative thin layer chromatography (aromatic compounds) or column chromatography with monitoring by TLC with DCQ for selective detection of the sulfur containing compounds or by GLC on 5% SE 30 on Chrom Q with flame ionization detection. Two monoalkylated products prepared as just described, are illustrated by reference compound #'s 26 and 27.

Similarly, R substituents with aromatic groups and including thiols may be prepared. Thus, for example, 4 mmol 4,4'-dimercaptophenyl ether is dissolved in 20 ml dry ethylene gylcol monomethyl ether and then 4 mmol sodium bicarbonate added. Four mmol of BTFA were then added under N$_2$ and the reaction allowed to stir for two days prior to work up by column chromatography, to yield the dialkylated compound illustrated by reference #35.

Examples VIII and IX below illustrate in vivo biological activity for several of the inventive compounds and with TFT and EPPAT also being tested for comparisons.

EXAMPLE VIII

T. ni larvae are treated with 1 or 2$\mu$ liters of ethanol, with TFPOS, wit o-ethyl-S-phenyl phosphoramidothiolate (EPPAT), or with 1,1,1-trifluorotetradecan-2-one (TFT) in 1$\times$10$^{-1}$M ethanol solutions on the dorsum of the thorax three times per day (4, 12 and 17 hr after lights on) during the first two days of the last larval stadium. The insects were held under standard rearing conditions (27° C., 14 hr light, 10 hr dark). The time of pupation was checked daily at 4 hr after lights on and the pupae were checked for successful emergence two weeks later.

TFPOS was effective in delaying the pupation of the larvae of T. ni when repeated doses of 0.1$\mu$ moles were applied during the first two days of the last larval stadium. The effects were more dramatic when doses of 0.2$\mu$ moles/application were used, which indicates a dose dependence. The irreversible inhibitor EPPAT also delayed preparation at both doses used, and appeared to be more potent than TFPOS. By contrast, neither dose of TFT resulted in a delay in pupation. No mortality was observed with repeated 1$\mu$ liter applications of ethanol, TFT or TFPOS, but with repeated applications of 2$\mu$ liters of ethanol, the TFT solution or the TFPOS solution (0.2 moles/application) resulted in 1, 6 and 4 percent mortality respectively.

EXAMPLE IX

Larvae were treated on the dorsum of the thorax with 1 or 2$\mu$ liters of ethanol (control) and with 1 or 2$\mu$ liters, respectively, of 10$^{-1}$M TFT, TFPOS, DTFT or EPPAT in ethanol, 3 times per day at 4, 12 and 17 h ALO (after lights on) on L5D1 and D2. Time of pupation was checked daily at 4 h ALO, and emergence was checked 2 weeks after treatment. L5D1 larvae 4 h ALO were also treated, but only once with 1$\mu$ liter ethanol or with 1$\mu$ liter of 10−1 M TFT, TFPOS, or EPPAT in ethanol, and then were bled at 1, 8, 12, 23, 28, or 32 h after treatment. Hemolymph was collected from five larvae, mixed and frozen at −60° C. until assayed for JHE and α-NAE activity. There was no difference in the time of pupation between control L5D1, L5D2 larvae treated with (1 and 2μ liters) of ethanol and larvae treated with 0.1 and 0.2μ mole of TFT. For the same doses of TFPOS, EPPAT and DTFT, pupation was delayed with respect to the controls in a dose-dependent manner. Death usually occured during the larval-pupal transformation, with the control mortality at 2μ liters of ethanol being 1%, TFT at 0.2M being 6%, an TFPOS being 4%.

The studies illustrated by Examples VIII and IX show that TFPOS and DTFT delayed the pupation of $T.$ $ni,$ but that TFT has no such in vivo effect. In another study, the in vivo inhibition of $T.$ $ni$ JHE following a single dose (0.1μ moles/larve) of EPPAT and TFPOS respectively was monitored. Maximum inhibition of $T.$ $ni$ JHE was obtained one hour after topical application for each.

Both TFPOS and DTFT appear to be more selective for JHE in vivo than EPPAT, and as effective with respect to the maximum percent inhibition obtainable after treatment. EPPAT, however, appears to be more persistent.

The drug clofibrate (α-[4-chlorophenoxy)-α-methylpropionate; Atromid-S) is one of a class of compounds given to heart patients as a hypolipidemic agent. Both the ethyl ester and the free acid seem to have biological activity, but the half-life of the drug is significantly increased by maintaining it as the ethyl ester. Under assay conditions where the $V_m$ of the hydrolysis of clofibrate is 104 nmol/min mg microsomal protein and the $K_m$ is 5.5 mM and the reaction is monitored by the release of ethanol using an alcohol dehydrogenase system, even low concentrations of compound #19 (which mimics the size of clofibrate) led to a significant delay in reacting maximal velocity. Wilkinson kinetics gave curves expected for a slowly reversible inhibitor. These data indicate the potential of the novel compounds to act as drug synergists.

The 1,1,1-trifluoro-3-substituted thiopropan-2-one moiety of the monoalkylated compounds may be attached to solid phases by a variety of coupling agents for affinity chromatography applications to purify desired hydrolytic enzymes and/or to separate them from biological fluids. Suitable solid phases include, for example, agarose, glass, and polyacrylamide. Suitable coupling agents, for example, include bifunctional coupling agents such as 4,4'-dimercaptobiphenyl, 4,4-dimercatophenyl ether, 1,2-dimercaptoethane and 1,3-dimercaptophopane.

For instance, following reaction of 1,4-butane dithiol or 1,10-decame dithiol with equimolar BTFA, the reaction mixture can be readily coupled with an epoxy activated agarose. Example X, below, illustrates a representative coupling procedure, and FIG. II the coupled product (wherein $R_1$ is a bivalent radical derived from the univalent R substituents of monoalkylated compounds as previously described).

EXAMPLE X

To 40 ml of gel in 28.5 ml 1N NaOH, 57 mg NaBH$_4$ and 5.71 mg of butane diglycidylether were added. The mixture was swirled for 4 hr at room temperature and then washed exhaustively with distilled water, followed by 0.1M sodium bicarbonate. 10 ml of the gel was placed in 10 ml of 0.1M sodium bicarbonate, and 4 mmol of butane dithiol (or decane dithiol), previously reacted with BTFA, added. The reaction mixture was shaken vigorously for 24 hr under N$_2$, then vigorously washed with dilute acetic acid in water, followed slowly up a gradient to complete ethanol. The coupled product was stored in anhydrous ethanol, and washed with an ethanol to distilled water and distilled water to buffer gradient before use. FIG. II below illustrates a representative coupled ligand prepared as just described, which will selectively bind esterases such as juvenile hormone esterase.

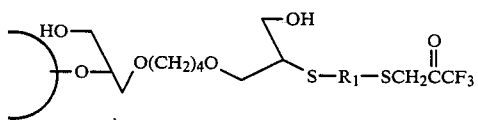

FIG. II

A variety of similar ligands can be prepared and coupled by several widely accepted techniques. For instance, the reaction products of BTFA with 4,4'-dimercaptohenyl ether, 4,4'-dimercaptobiphenyl, or 4-hydroxythiophenol can be substituted for the aliphatic dithiols. Alternatively, the reaction product of p-hydroxythiophenol with BTFA can be reacted with ethyl bromoacetate or hemisuccinate with dimethylaminopyridine catalyst and the resulting free acids attached to aminopropyl gel or attached directly with cyanuric acid chloride.

The differentiation between reversible and irreversible inhibitors can be tested by removal of the inhibitors from the enzyme inhibitor species by physical or chemical means. Since the exact structure of the $T.$ $ni$ JHE active site is lacking at the present time, the removal of inhibitor by physical means, i.e. gel filtration or dialysis, was used to demonstrate reversibility of inhibition for the novel compounds.

The results of removal by dialysis showed some loss in activity of the control enzyme in the first eight hours; however, the activity of a TFT inhibited and TFPOS inhibited-enzyme restored gradually to the same activity as in the uninhibited enzyme 48 hours after starting the dialysis. EPPAT, in contrast, was characterized by almost complete loss of enzyme activity even 48 hours after starting dialysis.

The stability of EPPAT inhibited $T.$ $ni$ to reactivation indicates that this compound is an irreversible inhibitor of $T.$ $ni$ JHE. On the other hand, TFT and TFPOS are reversible inhibitors of $T.$ $ni.$ JHE as their inhibited enzyme was totally regenerated by dialysis. However, the rate of reactivation seems to be slow, as the t$_{0.5}$ is more than 20 hours under the conditions utilized.

While the invention has been described in connection with specific embodiments thereof, it will be understood that it is capable of further modification, and this application is intended to cover any variations, uses or adaptations of the invention following, in general, the principles of the invention and including such departures from the preent disclosure as come within known or customary practice in the art to which the invention pertains and as may be applied to the essential features hereinbefore set forth, and as fall within the scope of the invention and the limits of the appended claims.

We claim:

1. A compound of the formula

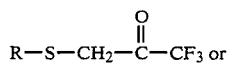

or

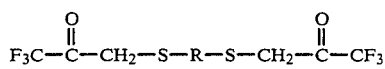

wherein R is a substituent having at least 5 multivalent atoms.

2. The compound as in claim 1 wherein the multivalent atoms of the substituent include a majority of carbons.

3. The compound as in claim 1 wherein the multivalent atoms of the substituent include nitrogen, selenium, sulfur, or oxygen.

4. The compound as in claim 1 wherein said substituent has from 4 to about 12 carbon atoms, and is an alkyl, alkenyl, alkynyl, aryl, or arylalkyl group.

5. The compound as in claim 1 of the formula

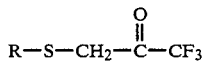

wherein R is an alkyl, alkenyl or alkynyl substituent having from 4 to about 12 carbon atoms and includes nitrogen, sulfur or oxygen therein.

6. The compound as in claim 5 wherein said compound inhibits at least one hydrolytic enzyme.

7. The compound as in claim 1 wherein said compound reversibly inhibits juvenile hormone esterase, alpha-naphtyl acetate, acetylcholinesterase, trypsin, alpha-chymotrypsin or neurotoxic esterase.

8. The compound as in claim 1 wherein R is an alkyl and includes a thiol.

9. The compound as in claim 1 wherein R is an alkyl, alkenyl or alkynyl and includes methoxy or acetoxy.

10. The compound

11. The compound

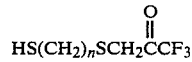

wherein n equals 4 to about 10.

12. A compound of the formula

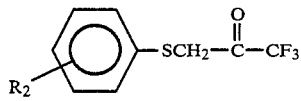

wherein $R_2$ is methyl, ethyl, propyl, butyl, methoxy or acetoxy.

13. A compound of the formula

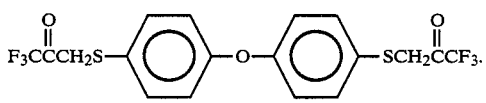

* * * * *